(12) United States Patent
Dai et al.

(10) Patent No.: US 10,575,956 B2
(45) Date of Patent: Mar. 3, 2020

(54) METHOD FOR OPTIMIZING IMPLANT DESIGNS

(71) Applicant: Zimmer, Inc., Warsaw, IN (US)

(72) Inventors: Yifei Dai, Warsaw, IN (US); Christine Schaerer, Winterthur (CH); Dwight T Todd, Fort Wayne, IN (US); Jeffrey E. Bischoff, Warsaw, IN (US); Adam D. Henderson, Winterthur (CH)

(73) Assignee: Zimmer, Inc., Warsaw, IN (US)

( * ) Notice: Subject to any disclaimer, the term of this patent is extended or adjusted under 35 U.S.C. 154(b) by 205 days.

(21) Appl. No.: 15/890,735

(22) Filed: Feb. 7, 2018

(65) Prior Publication Data

US 2018/0161166 A1    Jun. 14, 2018

Related U.S. Application Data

(62) Division of application No. 14/471,440, filed on Aug. 28, 2014, now Pat. No. 9,925,052.

(60) Provisional application No. 61/872,296, filed on Aug. 30, 2013.

(51) Int. Cl.
| | |
|---|---|
| *A61F 2/30* | (2006.01) |
| *A61F 2/38* | (2006.01) |
| *A61F 2/46* | (2006.01) |
| *A61B 5/107* | (2006.01) |

(52) U.S. Cl.
CPC ........ *A61F 2/30942* (2013.01); *A61F 2/3094* (2013.01); *A61F 2/38* (2013.01); *A61F 2/3859* (2013.01); *A61F 2/4684* (2013.01); *A61B 5/1076* (2013.01); *A61F 2/3868* (2013.01);
(Continued)

(58) Field of Classification Search
CPC ..... A61B 5/107; A61B 5/1072; A61B 5/1076; A61F 2/3094; A61F 2/30942; A61F 2/38; A61F 2/3859; A61F 2002/3863; A61F 2/3868; A61F 2/3886; A61F 2/4684
See application file for complete search history.

(56) References Cited

U.S. PATENT DOCUMENTS

| | | | |
|---|---|---|---|
| 8,187,280 B2 * | 5/2012 | May ................... | A61B 17/1764 606/88 |
| 9,131,945 B2 * | 9/2015 | Aram ................... | A61B 17/154 |

(Continued)

OTHER PUBLICATIONS

"U.S. Appl. No. 14/471,440, Notice of Allowance dated Nov. 13, 2017", 9 pgs.

(Continued)

*Primary Examiner* — Larry E Waggle, Jr.
(74) *Attorney, Agent, or Firm* — Schwegman Lundberg & Woessner, P.A.

(57) ABSTRACT

Methods are disclosed for designing a tibial implant to minimize cortical impingement of a keel or other fixation structure when the tibial implant is implanted in the tibia bone. The design of the keel or other fixation structure on the tibial baseplate can be based on determining a common area between defined cancellous regions of at least two tibia bones. Methods are disclosed for designing a femoral component having a stem extension such that the stem can be sufficiently placed in the diaphysis of the femur when the femoral component is implanted. The method includes determining a canal axis in a femur that creates adequate engagement between a reamer and the diaphysis of the femur.

9 Claims, 10 Drawing Sheets

(52) U.S. Cl.
CPC .............. *A61F 2002/30878* (2013.01); *A61F 2002/30884* (2013.01); *A61F 2002/3863* (2013.01)

(56) References Cited

U.S. PATENT DOCUMENTS

| | | | |
|---|---|---|---|
| 2004/0019383 A1* | 1/2004 | Beguec | A61F 2/4684 623/18.11 |
| 2013/0131820 A1 | 5/2013 | Wentorf et al. | |
| 2015/0066150 A1 | 3/2015 | Dai et al. | |

OTHER PUBLICATIONS

"U.S. Appl. No. 14/471,440, Response filed Aug. 16, 2017 to Restriction Requirement dated Jun. 30, 2017", 8 pgs.

"U.S. Appl. No. 14/471,440, Restriction Requirement dated Jun. 30, 2017", 6 pgs.

* cited by examiner

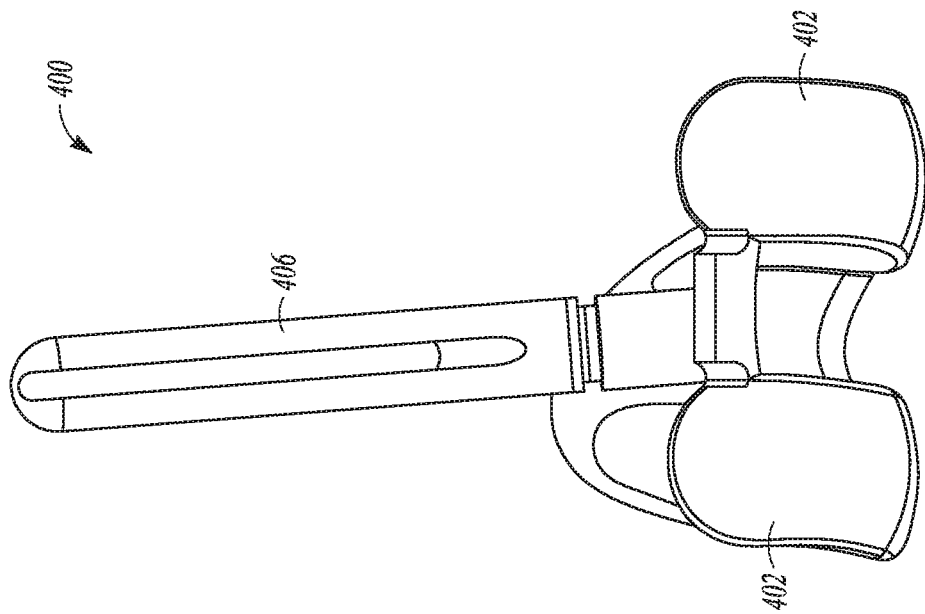
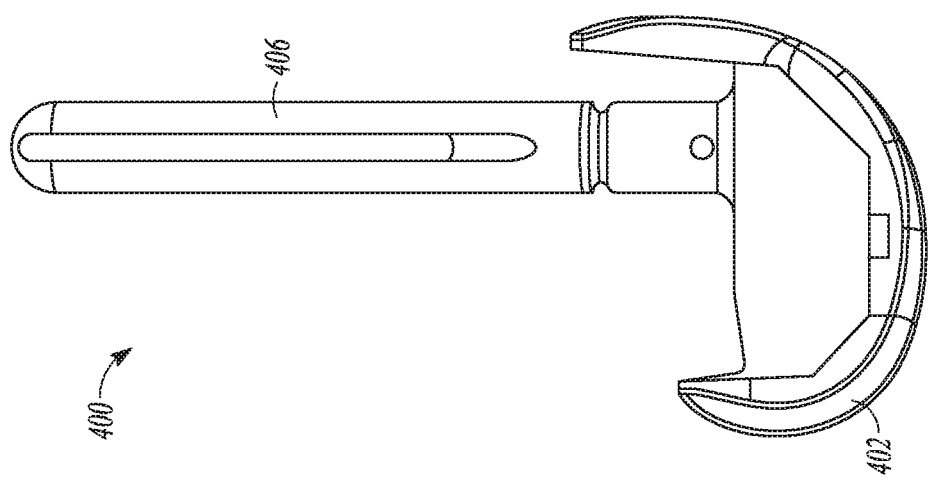

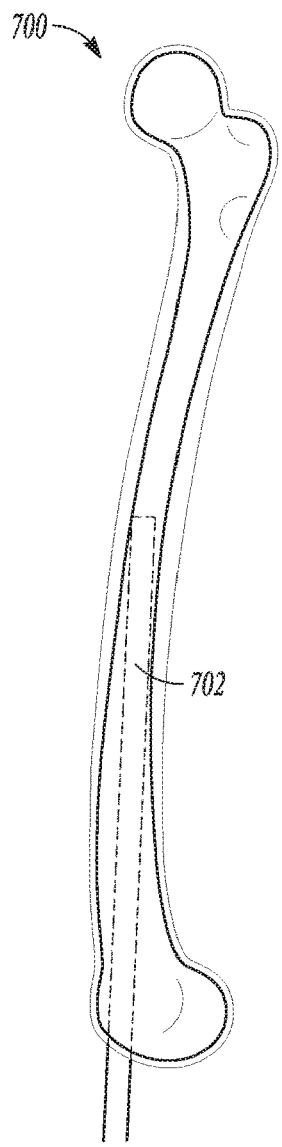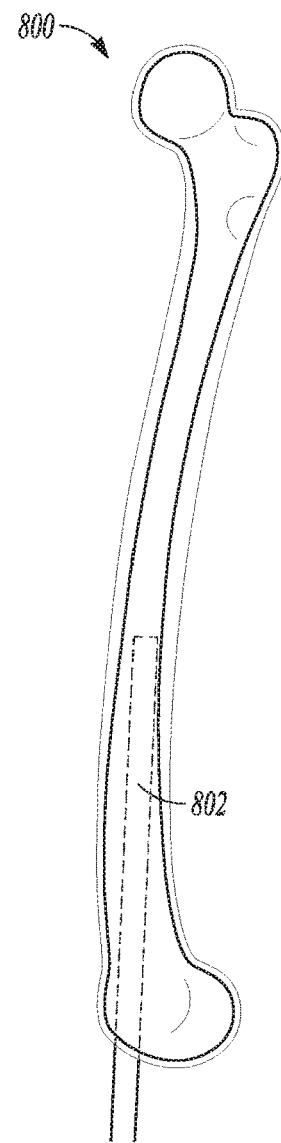
FIG. 11A  FIG. 12A
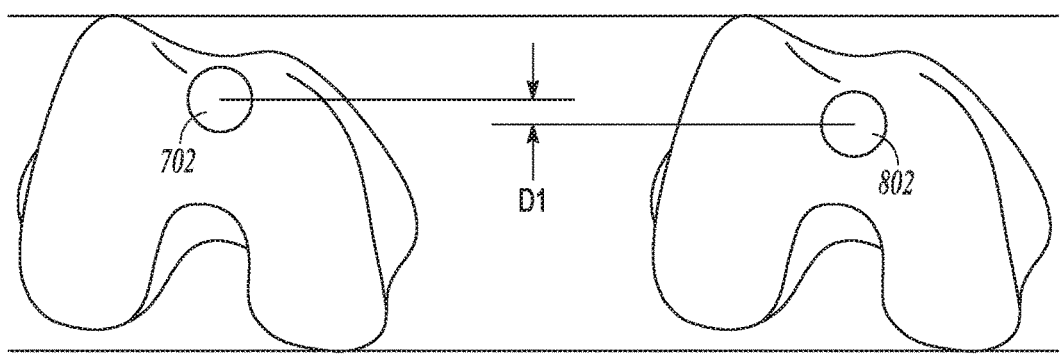
FIG. 11B  FIG. 12B

METHOD FOR OPTIMIZING IMPLANT DESIGNS

CLAIM OF PRIORITY

This application is a divisional of U.S. patent application Ser. No. 14/471,440, filed on Aug. 28, 2014, which claims the benefit of priority under 35 U.S.C. § 119(e) of U.S. Provisional Patent Application Ser. No. 61/872,296, filed on Aug. 30, 2013, each of which are incorporated by reference herein in its entirety.

TECHNICAL FIELD

The present patent application relates to orthopedic prostheses, and more particularly, to methods and systems for designing femoral and tibial components of a knee prosthesis.

BACKGROUND

Orthopedic prostheses are commonly utilized to repair and/or replace damaged bone and tissue in the human body. For a damaged knee, a knee prosthesis may be implanted using a proximal tibial baseplate component, a tibial bearing component, and a distal femoral component. The tibial baseplate component is affixed to a proximal end of the patient's tibia, which is typically resected to accept the baseplate component. The femoral component is implanted on a distal end of the patient's femur, which is also typically resected to accept the femoral component. The tibial bearing component is placed between the tibial baseplate component and the femoral component, and may be fixed or slidably coupled to the tibial baseplate component.

The tibial baseplate component provides support for the tibial bearing component. Forces generated by use of the knee prosthesis are transferred through the tibial bearing component to the tibial baseplate component, and ultimately to the tibia. In order to ensure long term performance of the knee prosthesis, stable and firm securement of the tibial baseplate component to the proximal end of the patient's tibia is desired. The tibial baseplate can include securement features, such as keels or pegs, which can improve fixation of the tibial component to the proximal end of the tibia.

The femoral component replaces the articular surfaces of one or both of the natural femoral condyles and can articulate with the tibial bearing component. A stem extension can be attached to or a part of the femoral component and can be configured for insertion in the femoral canal. The stem extension can provide stability for securement of the femoral component to the distal end of the femur.

OVERVIEW

The present inventors have recognized, among other things, an opportunity for improved placement of a keel, or other fixation structure, on a tibial baseplate in order to minimize impingement of the keel with an inner cortical surface of a patient's tibia after the tibial baseplate is secured to the tibia. The present inventors have recognized, among other things, an opportunity for improved placement of a femoral stem extension on a femoral component.

To better illustrate the systems and methods disclosed herein, the following non-limiting examples are provided:

In Example 1, a method of designing a tibial implant to minimize cortical impingement in a metaphyseal region of a tibia bone when the tibial implant is implanted in the tibia bone can include determining a reference point with respect to a location on a tibial tray of a provisional implant and placing the provisional implant on at least two tibia bones. The method can further include defining a two-dimensional cancellous region enclosed by metaphyseal cortex for each of the at least two tibia bones and determining a common area between the defined cancellous regions of the at least two tibia bones at the cross-section of a specific proximal-distal location on the at least two tibia bones. The method can further include determining a desired target region within the cancellous region of the at least two tibia bones for placement of a fixation structure of the tibial implant, and fabricating an implant comprising a tibial tray and a fixation structure configured to be attached to the tibial tray. With this method, the implant is configured such that, when implanted in a tibia bone having a comparable overall size to the at least two tibia bones, the fixation structure can be located within the desired target region for placement.

In Example 2, the method of Example 1 can optionally be configured such that defining the cancellous region enclosed by metaphyseal cortex includes determining at least three points on each of the at least two tibia bones bone that define an inner cortical surface of each of the at least two bones.

In Example 3, the method of Example 1 or 2 can optionally be configured such that determining the common area between the defined cancellous regions includes mapping the at least three points on each of the at least two tibia bones onto the two-dimensional coordinate system to create a polygon-shaped area for each of the at least two tibia bones.

In Example 4, the method of Example 3 can optionally be configured such that determining the common area further includes overlaying the polygon-shaped areas for each of the at least two tibia bones to find the common area.

In Example 5, the method of any of Examples 1-4 can optionally be configured such that the desired target keel region is defined by the common area subtracted by a radius of the fixation structure or a dimension of an instrument used in implanting the tibial implant.

In Example 6, a method of determining a canal axis that creates a best fit between a reamer and a diaphysis of a femur for preparing the femur for a femoral implant can include providing two or more cylinders having various diameters and representing reamers configured for use in preparing the femur for the femoral implant, and inserting a first cylinder, having a first diameter, into a canal of the femur to a predetermined reaming depth. If the reaming depth achievable with the first cylinder is less than the predetermined reaming depth, the method can include inserting the first cylinder into the canal to a maximum reaming depth that the first cylinder is able to fit in the canal. If the reaming depth achievable is about equal to or greater than the predetermined reaming depth and the first cylinder is not seated against an inner cortex of the femur, the method can include inserting a second cylinder, having a second diameter, into the canal of the femur to the predetermined reaming depth. The second diameter can be greater than the first diameter of the first cylinder. Cylinders of increasingly greater diameters can be inserted into the canal of the femur until a particular cylinder is seated in the canal. The method can further include determining an optimal cylinder position and an optimal canal axis can be based on a longitudinal axis of the optimal cylinder position.

In Example 7, the method of Example 6 can optionally further include adjusting an entry point for inserting the particular cylinder in the distal end of the femur in at least one of an anterior/posterior direction and a medial/lateral direction.

In Example 8, a method of designing a femoral component having a stem extension and configured for implantation on a distal end of a femur can include determining a canal axis of a plurality of femurs using at least one cylinder to create an optimal fit between a reamer and a diaphysis of each of the plurality of femurs. The plurality of femurs can have a comparable size and can be configured to correspond to one implant size of an implant family. The method can further include determining a position of the stem extension on the femoral component as a function of the determined canal axis of the plurality of femurs.

In Example 9, the method of Example 8 can optionally be configured such the position of the stem extension on the femoral component can be determined for each of the plurality of femurs and averaged to determine the position of the stem extension on the femoral component for a particular size in the implant family.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 8A is a side view of an example of a femoral component having a stem extension.

FIG. 8B is an posterior view of the femoral component of FIG. 8A.

FIG. 11A is a side view of a femur with a cylinder inserted in the canal of the femur.

FIG. 11B is a distal view of the femur and cylinder of FIG. 11A.

FIG. 12A is a side view of a femur with a cylinder inserted in the canal of the femur.

FIG. 12B is a distal view of the femur and cylinder of FIG. 12A.

DETAILED DESCRIPTION

Figure 1:
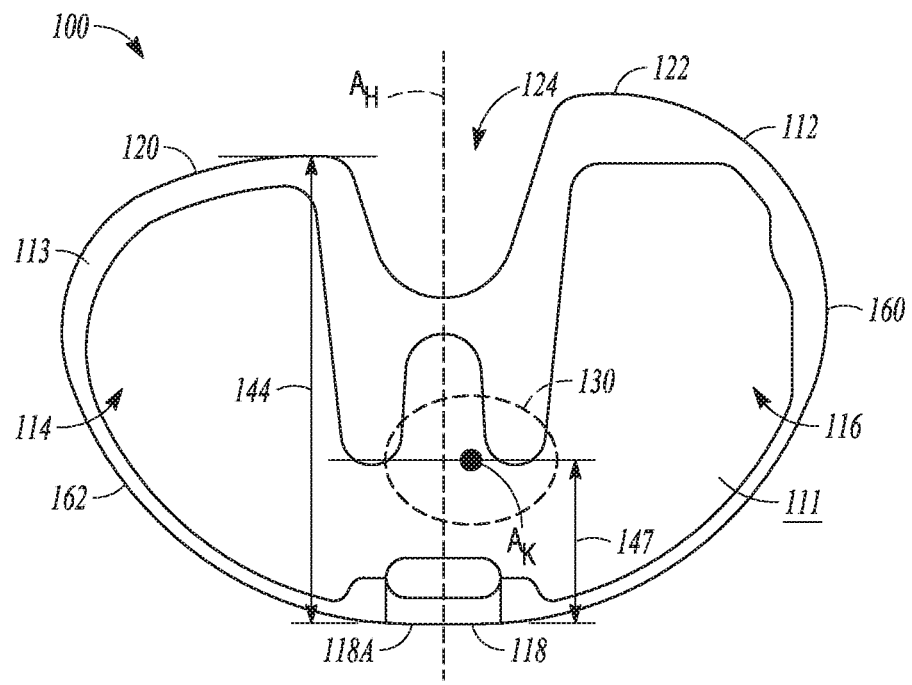
FIG. 1 is a top view of a proximal end of an example of a tibial baseplate.

The present application relates to systems and methods for designing a tibial baseplate with a fixation structure, such as a keel or a peg, configured to minimize impingement when implanted on a tibia. The tibial baseplate can be part of a knee prosthesis and the fixation structure can promote securement and/or stabilization of the tibial baseplate to a patient's proximal tibia. The present application relates to systems and methods for designing a femoral prosthesis component that can include a femoral stem. The femoral component can be part of a knee prosthesis and the femoral stem can promote securement and/or stabilization of the femoral component to a patient's distal femur, as part of, for example, a revision procedure.

A patient's tibia and/or femur can be prepared to receive the prosthesis component of the subject matter disclosed herein, by way of any suitable method or apparatus known by one of skill in the art. A surgical method can involve resection of the distal end of a patient's femur and/or resection of the proximal end of the patient's tibia. A method of resection can include forming a substantially planar resected surface of the femur and/or tibia. For a femoral component that includes a femoral stem, the surgical method can include preparation of the femoral intramedullary canal, through reaming, for receiving the femoral stem.

The term "proximal," as used herein, refers to the direction generally toward the torso of a patient. The term "distal," as used herein, refers to the direction generally away from the torso of a patient, or in the opposite direction of proximal. "Anterior," as used herein, refers to the general direction toward the front of a patient or a knee. As used herein, "posterior" generally refers to the direction toward the back of a patient or knee (the opposite direction of anterior). As used herein, "lateral" refers to the general direction away from the middle of the patient, and away from the sagittal plane. "Medial," as used herein refers to the general direction toward the middle of the patient and the sagittal plane, (the opposite direction of lateral). When used in reference to a knee, the term "lateral" refers to the general direction away from the patient's other knee, while "medial" refers to the general direction toward the patient's other knee.

With reference to the figures, some anatomical regions are labeled for clarity. In some figures, the anterior region of a tibia is labeled "A," the posterior region "P," the lateral region "L," and the medial region "M." In some figures, the anterior/lateral region of a tibia is labeled "AL," the posterior/lateral region is labeled "PL," the posterior/medial region is labeled "PM," and the anterior/medial region is labeled "AM."

Right and left knee prosthesis configurations are mirror images of one another about a sagittal plane. Therefore, regardless of the configuration depicted herein, is will be appreciated that the aspects of the prosthesis described are equally applicable to a right knee or left knee prosthesis.

1. Design of Tibial Baseplate, Including Placement of Fixation Support Structure(s)

FIG. 1 shows a proximal end of an example of a tibial baseplate 100 that can be used as a component in a knee prosthesis. The tibial baseplate 100 can include a proximal surface 111 configured to receive a tibial bearing component in a fixed or a sliding relationship. In an example, the baseplate 100 can include a raised rim 113 around the proximal surface 111 to receive surround, and hold the tibial bearing component therein; alternative structures can be used to receive and hold the tibial bearing component. The tibial bearing component can be configured to interact with a patient's distal femur or a femoral prosthesis component.

Figure 2:
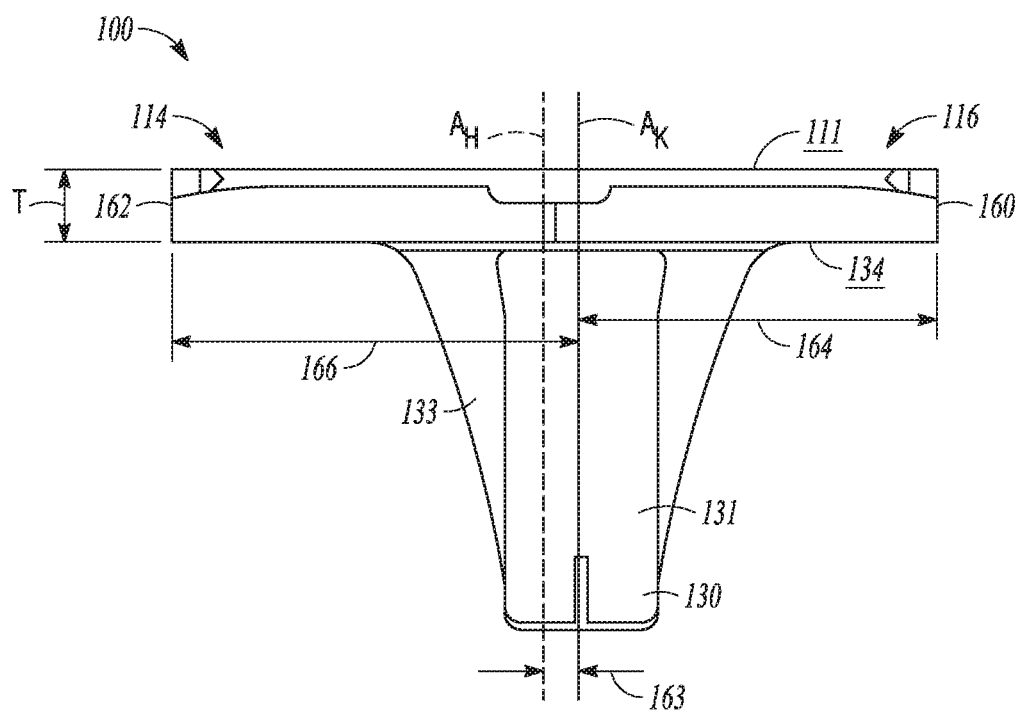
FIG. 2 is an anterior side view of the tibial baseplate of FIG. 1.

The tibial baseplate 100 can include an outer periphery 112, which can have a thickness T in a proximal/distal direction (see FIG. 2). The outer periphery 112 of the tibial baseplate 100 can form part of the tibial baseplate 100 referred to as the tibial tray. The outer periphery 112 can be defined by an anterior face 118, a posterior/lateral face 120, a posterior/medial face 122, a PCL cutout area 124, a lateral face 162 and a medial face 160. The tibial baseplate 100 can also include a lateral compartment 114, a medial compartment 116, and an anterior-posterior home axis $A_H$ separating the lateral 114 and medial 116 compartments. The anterior face 118 can include a linear or flat portion 118a that can be generally central located between lateral 114 and medial 116 compartments. The flat portion 118a can define an anterior-most extent of the tibial baseplate 100. As shown in FIG. 1, the tibial baseplate 100 can be side specific and can be asymmetric, such that the lateral 114 and medial 116 compartments can be different in size and/or shape.

FIG. 2 shows the side of the tibial baseplate 100, which can include a single fixation structure, a keel 130, which can extend distally from a distal surface 134 of the tibial baseplate 100 and into a tibia. The keel 130 can be monolithically or integrally formed as part of the tibial baseplate 100 or the keel 130 can be separately attachable to the distal surface 134 of the tibial baseplate 100. The keel 130 can have a cylindrical core 131 defining a longitudinal axis $A_K$ and having two or more fins 133 extending radially outwardly therefrom, and the fins 133 can be arranged symmetrically relative to the cylindrical core 131. The distal surface 134 can be the surface which contacts a resected surface of a patient's tibia after the baseplate 100 is implanted, at which point the keel 130 can extend into a cancellous region of the metaphysic or intramedullary canal of the tibia.

The keel 130 can be asymmetrically disposed on the distal surface 134 with respect to the home axis $A_H$. In an example, the longitudinal keel axis $A_K$ can be biased medially with respect to a vertical plane that contains home axis $A_H$—in other words, the keel axis $A_K$ can be offset toward the medial compartment 116 and away from the lateral compartment 114 by offset distance 163. Thus, a medial distance 164 between the keel axis $A_K$ and the medial-most portion of the medial face 160 can be less than a lateral distance 166 between the keel axis $A_K$ and the lateral-most portion of the lateral face 162.

As shown in FIG. 1, an anterior/posterior keel distance 147 can be measured posteriorly from the flat portion 118a of the anterior face 118 to the keel axis $A_K$, for example. A lateral depth 144 of the lateral compartment 114 can be measured posteriorly from the flat portion 118a of the anterior face 118 to the posterior/lateral face 120 of baseplate 100 in FIG. 1. The lateral depth 144 can exceed keel distance 147.

Figure 3:
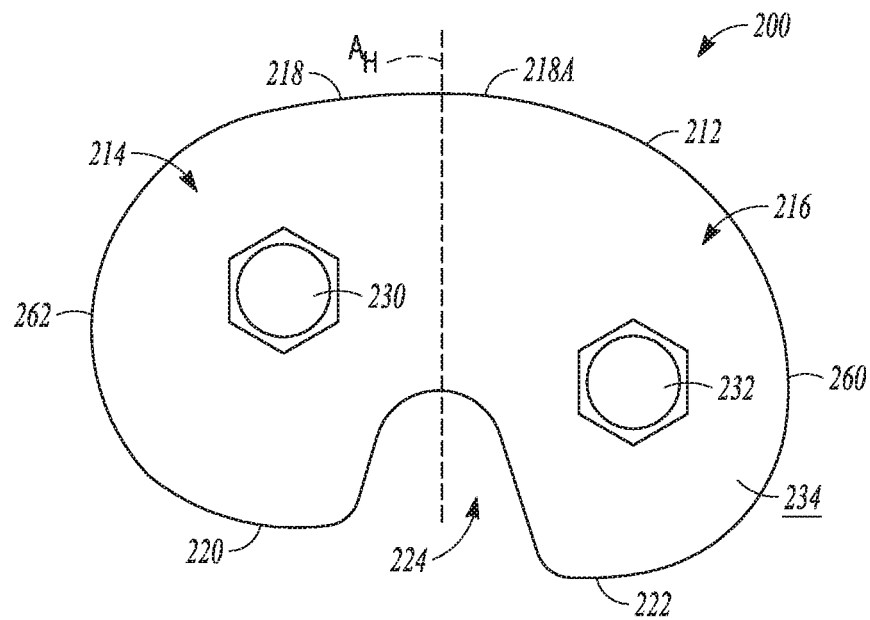
FIG. 3 is a bottom view of a distal end of another example of a tibial baseplate.

FIG. 3 shows a distal surface of an example of a tibial baseplate 200 that includes two fixation structures instead of the keel 130 of the tibial baseplate 100 of FIGS. 1 and 2. The proximal surface (not shown) of the tibial baseplate 200 can be similar to the proximal surface 111 of the tibial baseplate 100 and the outer periphery 212 can include the same elements.

The tibial baseplate 200 can include a lateral fixation peg 230 and a medial fixation peg 232, that can each extend distally from a distal surface 234 of the tibial baseplate 200 and into a cancellous region of the metaphysis or intramedullary canal of the tibia. In an example, the lateral 230 and medial 232 fixation pegs can be asymmetrically arranged about the anterior-posterior axis $A_H$.

Figure 4:
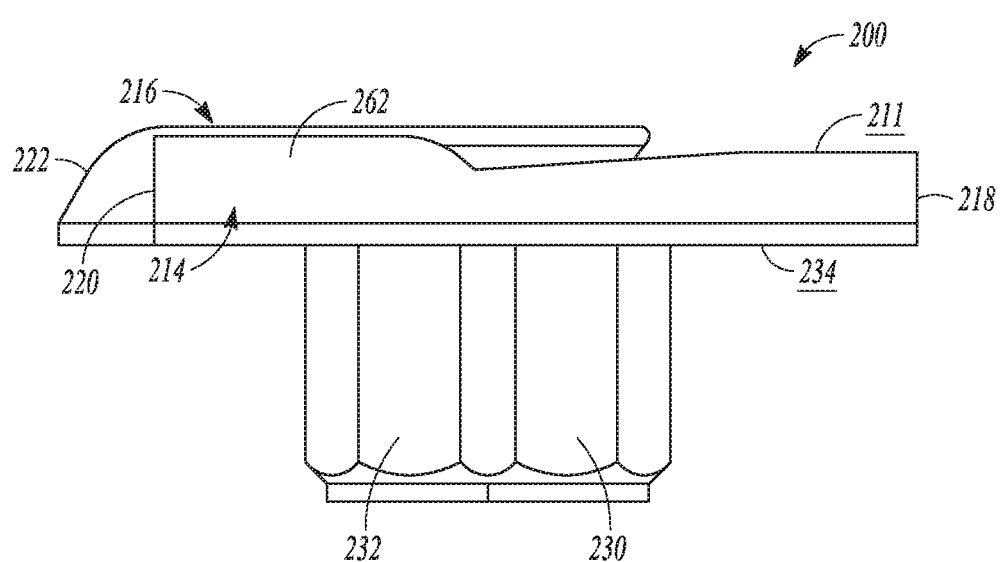
FIG. 4 is a lateral side view of the tibial baseplate of FIG. 3.

FIG. 4 shows the side of the tibial baseplate 200. In an example, the fixation pegs 230 and 232 can be hexagonal in cross-section near the distal surface 234 and can transition to a circular cross-section as the pegs 230 and 232 extend away from the distal surface 234.

The fixation structures of the tibial baseplates 100 and 200 (the keel 130 and the pegs 230 and 232, respectively) can be designed such that when the tibial baseplates 100 and 200 are implanted on a resected tibia, impingement with surrounding bone can be minimized. The present application discloses systems and methods for such design of the fixation structure on the tibial baseplate. Although the tibial baseplate 100 includes a keel 130 and the tibial baseplate 100 includes two fixation pegs 230 and 232, it is recognized that additional or alternative fixation structures can be use with a tibial baseplate and are within the scope of the present application. For example, instead of two fixation pegs, a tibial baseplate can be designed to have four fixation pegs.

Reference is made to a co-pending application, U.S. Ser. No. 13/593,339, Publication No. US 2013/0131820, and entitled "TIBIAL BASEPLATE WITH ASYMMETRIC PLACEMENT OF FIXATION STRUCTURES," for further disclosure on the tibial baseplate and the fixation structures described herein.

A method is described below for designing a tibial implant to minimize cortical impingement in a metaphyseal region when a tibial implant is implanted on a tibia. In an example, the method can be used to determine a "sweet spot" or area for placing the fixation structure on the tibial tray such that, for that particular implant size, cortical impingement can be reduced or eliminated.

Figure 5:
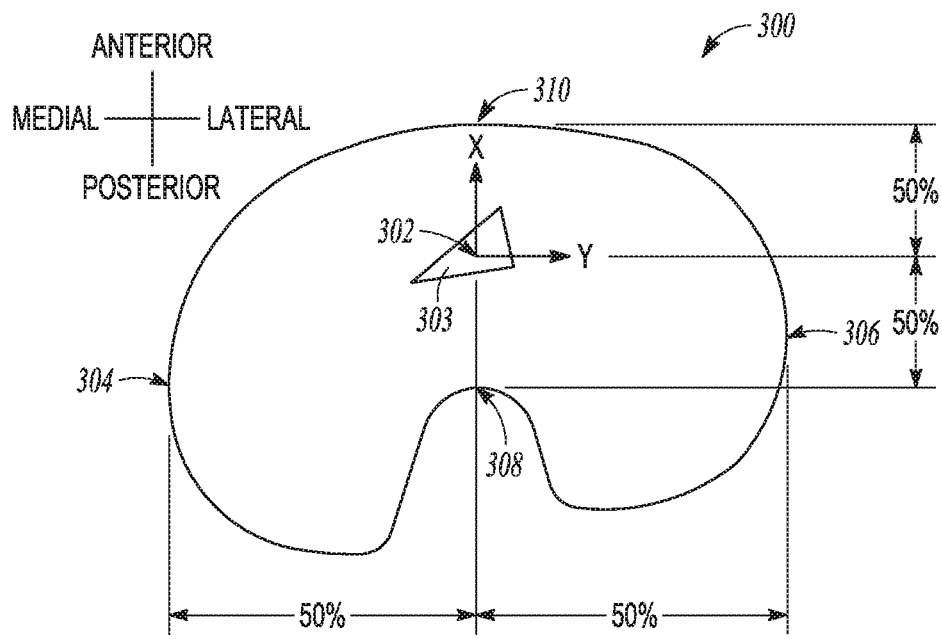
FIG. 5 is a top view of an outer periphery of an example of a provisional implant and its use in creating a two dimensional coordinate system.

The method can include creating a coordinate system that corresponds to a location on a tibial baseplate for each size implant in a tibial implant family. FIG. 5 shows an example of a provisional baseplate 300 having an outer periphery that is shaped similarly to the tibial baseplates 100 and 200 described above. A reference point 302 on the provisional baseplate 300 can be used as an origin for the coordinate system. In an example, the reference point 302 can be based on an anterior/posterior position on the provisional baseplate 300 and a medial/lateral position on the provisional baseplate 300. The reference point 302 can be based on an intersection of (1) a first mid-point between a medial-most point 304 and a lateral-most point 306 on the provisional baseplate 300, and (2) a second mid-point between an anterior-most point 308 and a posterior-most point 310 on the provisional baseplate 300. The reference point 302 can be the origin for an x-y coordinate system.

As described further below, a 'sweet spot' 303 can be created by placing the provisional baseplate 300 on at least two resected tibia bones, measuring three points on the resected tibia and then plotting those three points for each measured bone using the reference point 302 on the provisional baseplate 300. (Note that the 'sweet spot' 303 of FIG. 5 is exemplary and is not based on actual data.) The three points can correspond to a two-dimensional cancellous region of the tibia bone at a specific proximal-distal location. The cancellous region, which can be enclosed by metaphyseal cortex, can be used to determine the inner cortical surface of the tibia bone, which can define the cancellous region of the metaphysis or intramedullary canal.

The three data points can result in formation of a triangle in which each bone has an x1,y1 data point, an x2,y2 data point, and an x3,y3 data point. By plotting the three data points for each bone, and forming a triangle for each bone, a common area or 'sweet spot' between the triangles (like the exemplary sweet spot 303 of FIG. 5) can be determined. In other examples, more than three data points can be used, in which case the mapped data points can create another type of polygon shape instead of the triangle shown in FIG. 5.

This method can be done for each size of a tibial baseplate—at least two bones that correspond to each tibial baseplate size can be measured and the data plotted to determine the 'sweet spot'. These measurements can be performed on numerous bones. In an example, forty to fifty bones can be measured for each tibial baseplate size. In other examples, more or less bones can be measured for each tibial baseplate size. The measurements can be performed on actual bones and/or using digital bone data.

Figure 6:
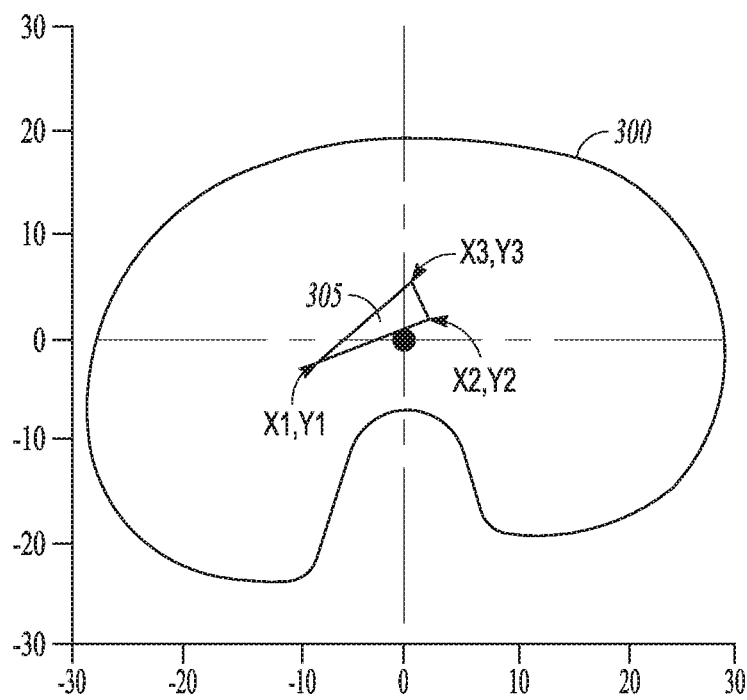
FIG. 6 is a plot of the two dimensional coordinate system illustrating a determined 'sweet spot' for keel placement.

FIG. 6 shows the provisional baseplate 300 of FIG. 5 and the coordinate system described above, as well as an example of a triangle or 'sweet spot' 305 formed for one size of a tibial baseplate. The 'sweet spot' 305 can be used to determine where a keel can be implanted in the cancellous region of the metaphysic or intramedullary canal to minimize impingement, and in turn, where the keel can be located on the tibial tray of the provisional baseplate 300, which can correspond to the keel's location on a tray of the tibial implant. By finding a common area for multiple bones that correspond to the same size tibial baseplate, if the placement of the keel of the tibial tray is based on the common area, impingement can be minimized or reduced when the tibial baseplate is implanted.

Moreover, because the common area or sweet spot can be based on multiple resected bones, the common area can also include resected tibias having surgical variability among them. For example, the multiple resected bones can include bones having varying degrees of resection slope and/or bones having varying degrees of implant placement rotation and overhang. Thus this methodology can result in minimizing or reducing impingement even in the presence of surgical variability.

In an example, the sweet spot can be a region where a center point on the keel can be placed and have little to no impingement. Since this sweet spot can be based on measurements taken, for example, at the cortex of the bone, the sweet spot can potentially place the center point of the keel near the cortex in some instances, in which case the external surfaces of the keel could cause some impingement at that region. Thus the desired target region for placement of the keel can be based on the common area and adjusted to account for the overall size and shape of the keel, which can be used in designing the keel's location on the tibial tray. The sweet spot or common area can be reduced by a radius or other characteristic dimension of the keel (or other fixation structure). In an example, instrumentation can be used during implantation—such as a broach—which can be larger in size than the keel, in which case the common area can be reduced by the size of such instrumentation.

Figure 7A:
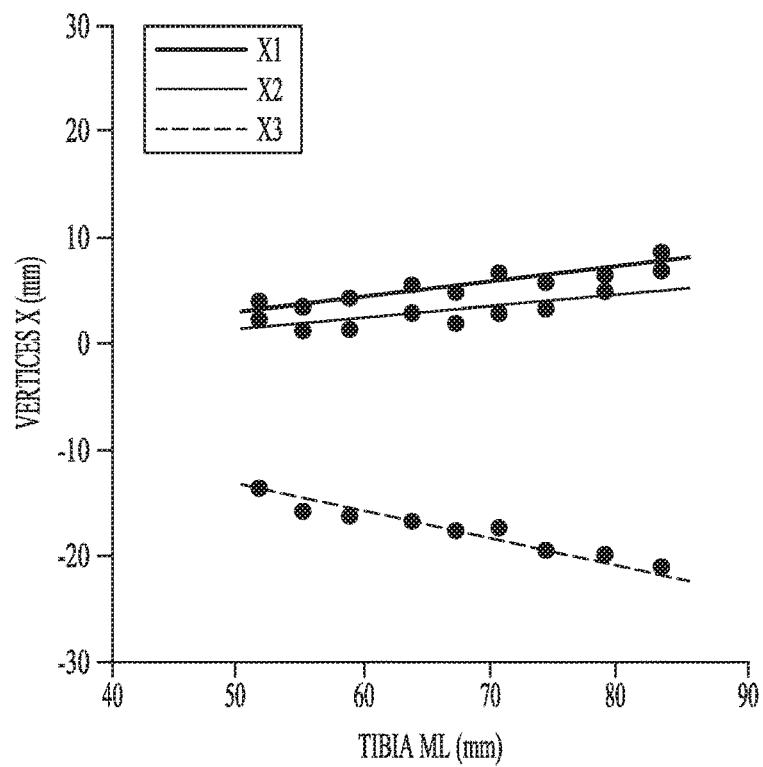
FIG. 7A is a plot of the x-values that form the sweet spot for each of nine implant sizes.
Figure 7B:
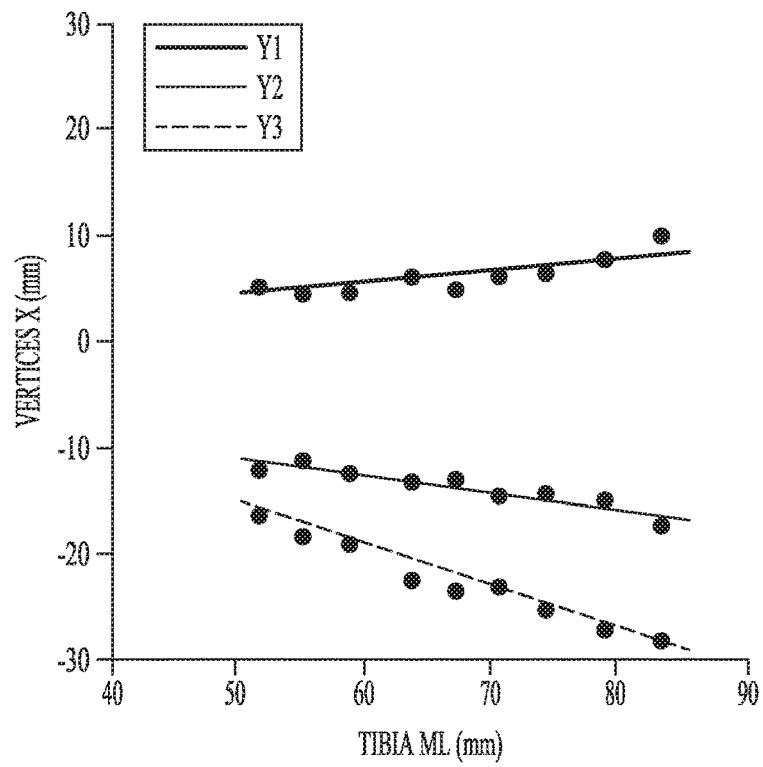
FIG. 7B is a plot of the y-values that correspond to the x-values of FIG. 7A.

FIGS. 7A and 7B show examples of data collected using the method described above. FIG. 7A shows the three x values (x1, x2, x3) for each of nine implant sizes, and FIG. 7B shows the three y values (y1, y2, y3) for the nine implant sizes of FIG. 7A. When the three data points (x1,y1; x2,y2; x3,y3) are plotted for each implant size, it represents a sweet spot for each implant size. The values shown in FIGS. 6, 7A and 7B represent a set of exemplary data. It is recognized that different data will be collected depending on, for example, how and where the measurements are taken on the bone, and the configuration of the tibial baseplate that the fixation structure is intended to be used with.

The method described above offers a design of a tibial baseplate in which a keel, or other fixation structure, can be located on the tibial baseplate in such a way that the fixation structure will have little to no impingement with the cortical bone. Due to the methodology used to determine the sweet spot for locating the keel or other fixation structures on the tibial baseplate, the keel design can accommodate surgical variability, such as, for example, a range of resection slopes.

The method was described in the context of a tibial baseplate having a keel, similar to a design of the tibial baseplate 100 of FIGS. 1 and 2. The method can also be used for a tibial baseplate having alternative fixation structures, such as for example, the two pegs 230 and 232 of the tibial baseplate 200. The methodology can be generally similar—measurements can be taken using tibial baseplates and at least two bones that correspond to each implant size. For the two pegs 230 and 232, two 'sweet spots' or common areas for each implant size can be determined—each sweet spot can correspond to one of the pegs 230 and 232.

2. Design of Femoral Component, Including Stem Housing

FIGS. 8A and 8B show an example of a femoral component 400 that can be used in a knee prosthesis. The femoral component 400 can be specific to either a right or left leg. The femoral component 400 can include condyles 402 that can be configured to articulate with a proximal end of a tibia bone or a tibial implant. The femoral component 400 can include a stem 406 that can extend from a non-articulating portion of the femoral component 400 and can be configured for placement in a canal of a femur. The use of a femoral stem, like femoral stem 406, and sufficient placement of the stem in the canal can improve the fixation stability from a knee arthroplasty, including a revision total knee procedure.

A method is described for designing a femoral stem on a femoral component using a plurality of femoral bones.

A. Analyzing Femoral Canal to Determine a Reamer/Canal Axis

A reamer can be used to prepare a femoral canal for receiving the stem 406 when the femoral component 400 is implanted on the distal end of the femur. Deep reaming of the canal can be important for achieving diaphyseal engagement, especially when the femoral stem 406 is configured for a press-fit. In an example, it can be desirable to ream to a depth of about 200 mm.

Figure 9A:
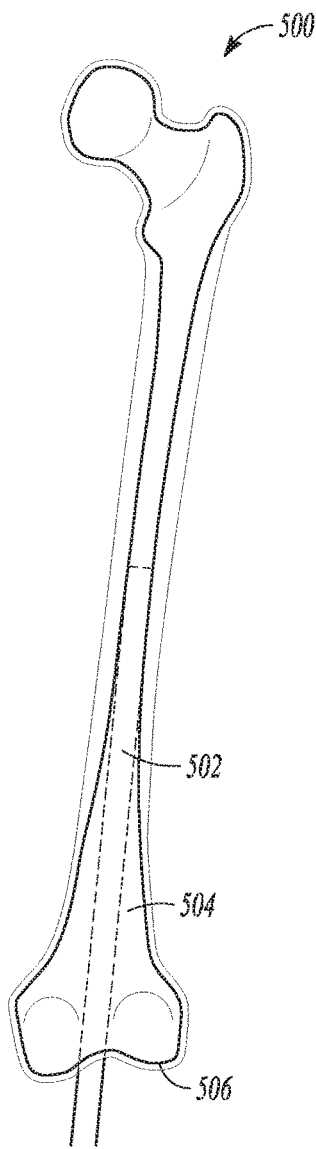
FIG. 9A is an anterior view of a femur with a cylinder inserted in the canal of the femur.
Figure 9B:
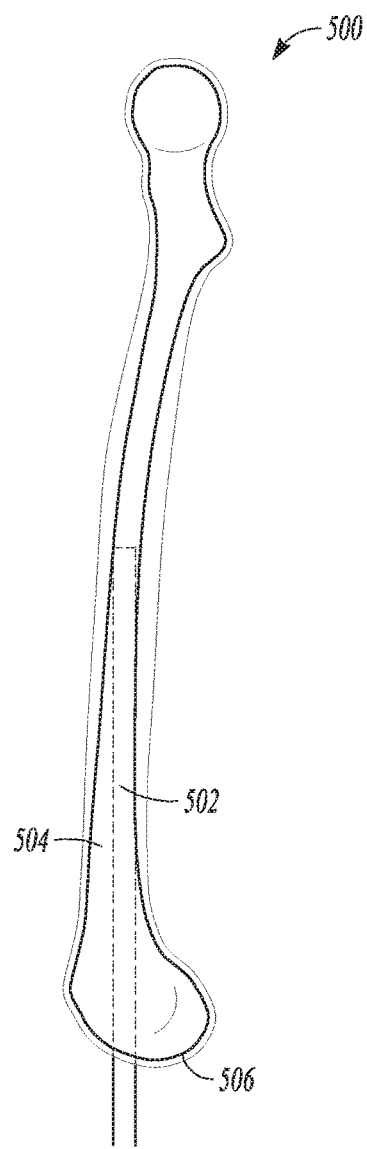
FIG. 9B is a side view of the femur and cylinder of FIG. 9A.
Figure 9C:
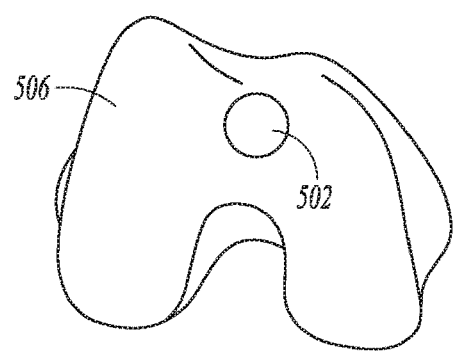
FIG. 9C is a distal view of the femur and cylinder of FIG. 9A.

FIGS. 9A and 9B show a femur bone 500 with a cylinder 502 (which can represent a reamer) inserted into a diaphysis 504 of the femur 500. FIG. 9C shows a distal end 506 of the femur 500 and an entry location of the cylinder 502 on the distal end 506. In an example, as shown in FIGS. 9A-9C, the cylinder 502 can have a diameter of about 10 mm.

To determine the reamer/canal axis, a method can be performed on multiple bones. The method can be performed virtually, for example, using a digital library of bones, or it can be performed manually using femur bones and one or more cylinders having various diameters and representing reamers configured for use in preparing the femur for the femoral implant. First, a user can create a best fit between a cylinder and the diaphysis of the femur, up to a particular predetermined reaming depth, such that the cylinder can be seated against the inner cortex and can be held in place. In an example, the predetermined reaming depth can be about 200 mm. In an example, the predetermined reaming depth can be about 150 mm. Other depths less than 150 mm and greater than 200 mm can be used as the predetermined reaming depth.

In the method described herein, the predetermined reaming depth is 200 mm. The method can include maximizing a diameter of a cylinder to contact the endosteal walls of the canal up to the 200 mm reaming depth. In an example, if a smallest reamer in a set of reamers has a diameter of 10 mm, the smallest cylinder in the set of one or more cylinders can have a diameter less than or about 10 mm. If the smallest cylinder is inserted into the canal and the reaming depth of 200 mm is not achieved, the method can include reducing the reaming depth of the cylinder until the cylinder can fit in a canal of the femur. Once the cylinder is properly seated at a maximum ream depth achievable, the optimal cylinder position can be determined.

On the other hand, if the smallest cylinder (in an example, 10 mm diameter cylinder) can achieve a reaming depth of about 200 mm or greater and the cylinder is not seated against an inner cortex of the femur or does not have sufficient contact with the walls of the canal at the reaming depth, a second cylinder having a greater diameter can be inserted into the canal, up to a reaming depth of about 200 mm. Cylinders having increasingly greater diameters can be inserted into the canal until sufficient seating or orientation of the cylinder in the canal is achieved. In an example, the cylinders can have increasingly greater diameters at 1 mm increments.

The method of determining the reamer/canal axis can include adjusting an entry point for inserting the particular cylinder in the distal end of the femur. The entry point can be adjusted in an anterior/posterior direction and/or a medial/later direction. In an example, the entry point can move within a square location 0-10 mm anterior and ±5 mm medial/lateral to a center of the femur, such that the square can create the boundaries of the entry point region. The entry point can be adjusted, for example, to account for different bone shapes. The method can also include having two or more users verify the appropriateness of the determined reamer/canal axis during a surgical procedure. Using the method steps above, a user can determine a reamer/canal axis which determines where the reamer or cylinder enters into the femur at the distal end.

Figure 10A:
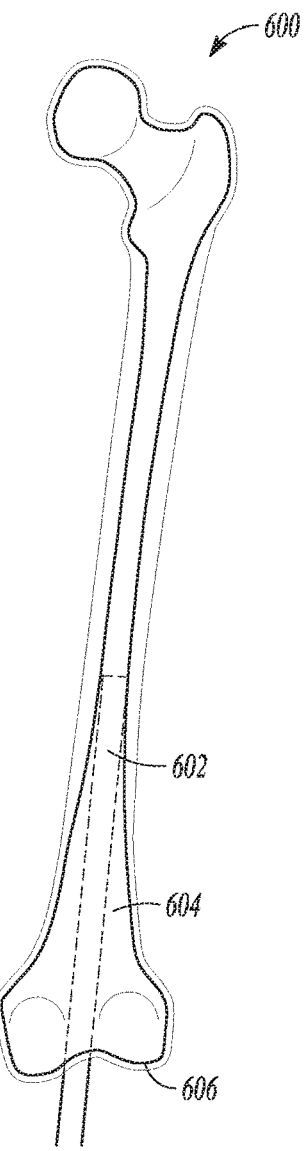
FIG. 10A is an anterior view of a femur with a cylinder inserted in the canal of the femur.
Figure 10B:
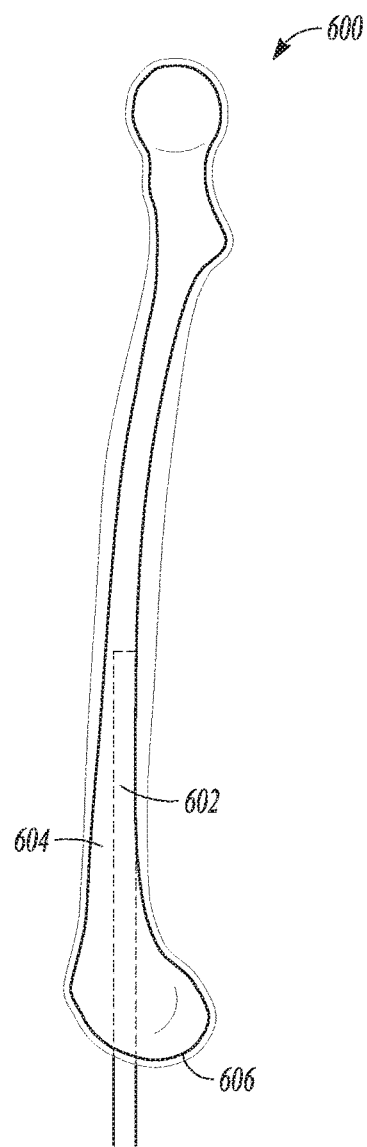
FIG. 10B is a side view of the femur and cylinder of FIG. 10A.
Figure 10C:
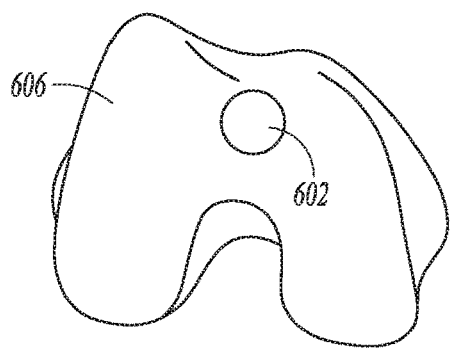
FIG. 10C is a distal view of the femur and cylinder of FIG. 10A.

FIGS. 10A-10C show a femur bone 600 with a cylinder 602 having a diameter of about 11 mm inserted into a diaphysis 604 of the femur 600 up to a depth of about 170 mm. A narrowing of the diaphysis or canal 604 of the femur 600 can prohibit a minimum 10 mm cylinder at a 200 mm reaming depth as performed in the femur 500 of FIGS. 9A and 9B. Thus a larger diameter cylinder 602 can be used, and the depth of insertion can be reduced, as compared to the femur 500 of FIGS. 9A and 9B. An entry location of the cylinder 602 on a distal end 606 of the femur 600 is shown in FIG. 10C.

FIG. 11A shows an original reamer depth and an originally determined entry point of a cylinder 702 into a femur 700. FIG. 12A shows an adjusted reamer depth and adjusted entry point of a cylinder 802 into a femur 800 based on an excessive anterior location caused by a femoral bow of the femur 800. FIGS. 11B and 12B illustrate a difference D1 between the entry points of each of the cylinders 702 and 802 shown in FIGS. 11A and 12A, respectively. An increased reaming depth can lead to an anterior shift of the distal entry point.

The method of determining the reamer/canal axis can be performed on numerous bones to collect data that can represent the variations between femur bones from patient to patient. As described above, the method can include using various cylinders having different diameters, and adjusting the reaming depth and/or the entry point to find effective positioning of the cylinder.

In an example, the method of determining the canal or reamer axis can include virtual remaining as mentioned above, and a reaming algorithm. The algorithm can maximize certain factors and conditions, and minimize others. For example, the algorithm can maximize reamer diameter and optimize engagement with the inner diaphysis of the femur. The target reaming depth can be set to 200 mm and if that is not feasible for a particular femur, the reaming depth can be shortened at 5 mm intervals until the canal of the femur can accommodate the reamer.

B. Determining Position of Femoral Stem Housing

The method described above for determining a canal axis for reamer placement can be used in designing a stem housing on a femoral implant. The method for designing the stem housing can include locating an anterior cortex 907 on a femur 900 (a second reference point on an outside of the femoral bone where a saw blade cuts an anterior surface of the femur) and measuring a distance D2 from the anterior cortex 907 to a canal/reamer axis 910 at a proximal/distal location, as shown in FIG. 13.

A distal cut plane or resection plane 914 can be used as a reference for determining the proximal/distal location for measuring the distance D2. In an example, the distal cut plane 914 can correspond to a distal femoral cut of 11 mm–a 9 mm primary distal resection with about 2 mm of bone loss. In an example, the distance D2 can be measured at a location about 40 mm proximal to the distal cut plane 914. The method for determining a position of the femoral stem housing can include applying the measured distance D2 to a femoral implant by locating an axis of the stem housing on the femoral component the distance D2 from an anterior flange of the femoral component.

Figure 13:
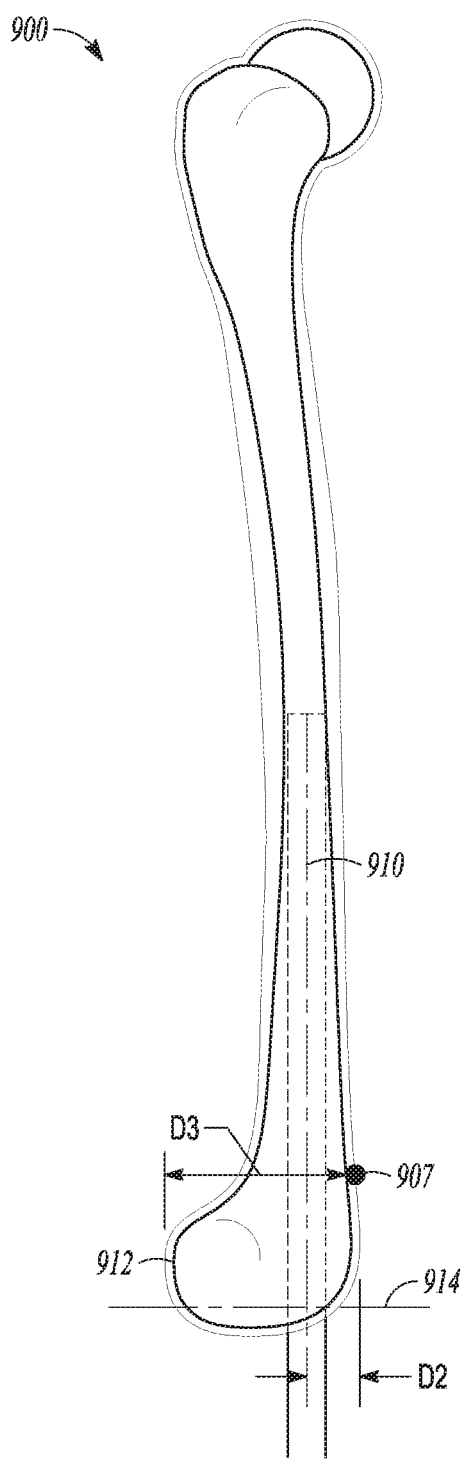
FIG. 13 is a side view of a femur with a cylinder inserted in the canal of the femur.

FIG. 13 also includes a distance D3 which corresponds to an overall bone size and is defined as the distance between the anterior cortex 907 and a plane tangent to posterior condyles 912. The distance D3 can also be referred to as a functional AP dimension (fAP or FAP).

Similar to the method described under Part A for the canal axis, this methodology for the stem housing can be performed for each individual bone, including, in an example, multiple bones contained in a digital library of bones. Based on the measurement gathered for each bone, a location of the femoral stem on the femoral implant can be determined. The measurement for each bone can be used to create a patient database for determining a design of the stem housing that can best fit a canal of a patient's femur. The data can be averaged, based on, for example, a size of the femur and/or the femoral component.

Figure 14A:
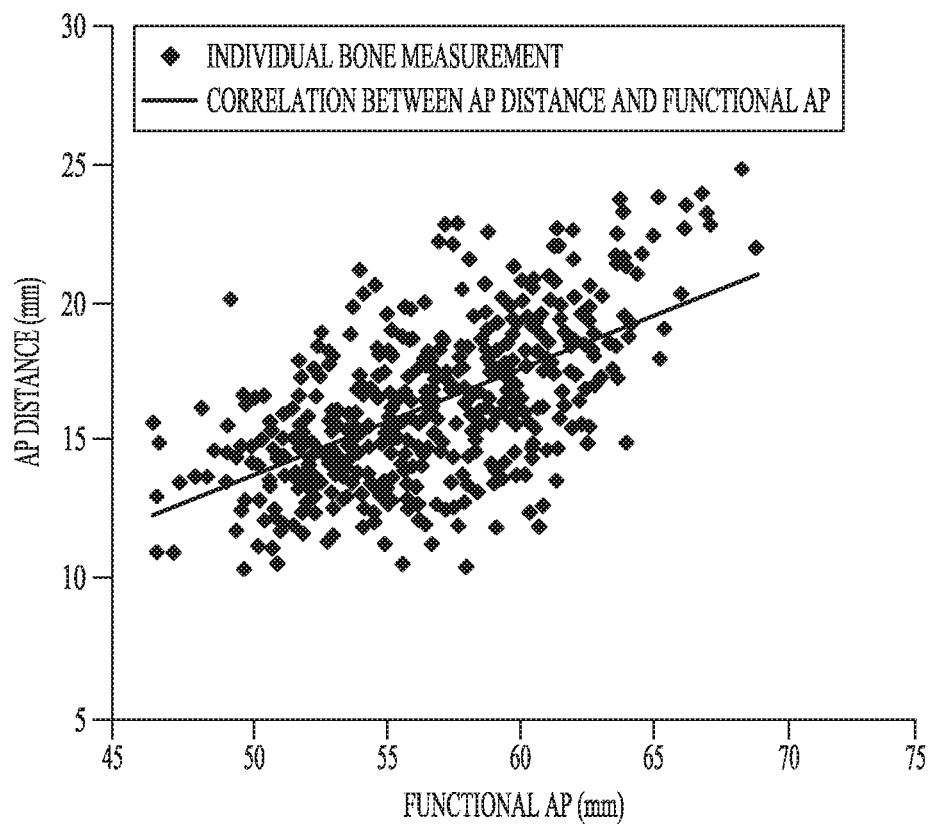
FIG. 14A is a plot of an anterior offset as a function of femur size as measured for individual bones.
Figure 14B:
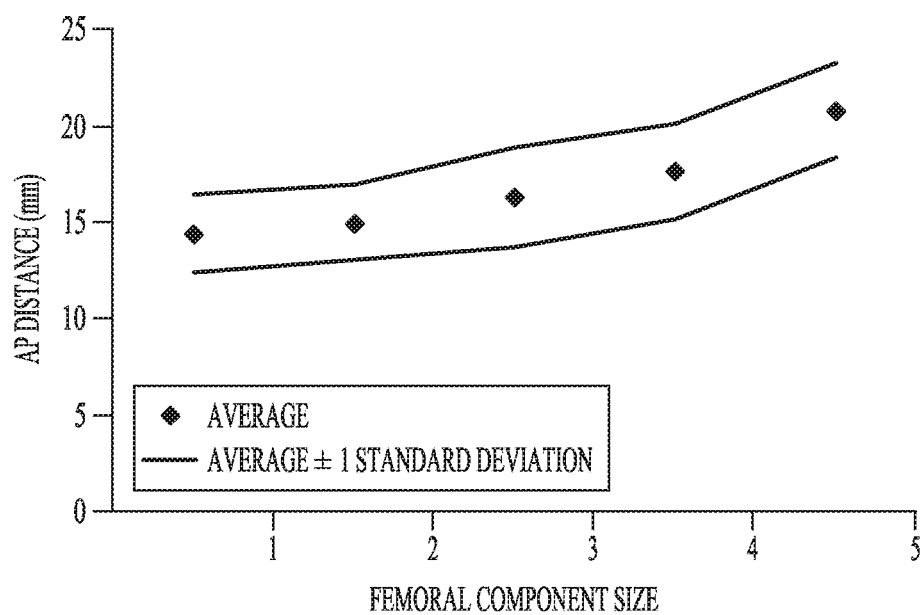
FIG. 14B is a plot of an anterior offset of a femoral stem on the femoral component as a function of femoral implant size.

FIG. 14A shows the anterior/posterior (AP) distance as a function of overall bone size (functional AP) for bones of different sizes. (See FIG. 13 defining these dimensions.) Since the bone size determines the implant size, this data can be used to determine the offset in design of the femoral stem. FIG. 14B shows the average measurement of a housing offset of the femoral stem for various sizes of femoral components in the implant family—larger offset values correspond to a more posterior position on the femoral component. Thus the design of the femoral stem, and its location on the femoral component, can be tailored for each femoral implant size. Because the collected data is based on an average of measurements collected on individual bones, in designing the femoral stem, the designer can select a location within the band shown in FIG. 14B of the average value plus or minus one standard deviation. As shown in FIG. 14B, as the implant size increases (to correspond to a larger femur size), the position of the stem on the femoral component is more posterior. Thus the femoral implants can be designed such that the anatomical stem housing can be positioned more anterior for smaller femurs and more posterior for larger femurs.

By using data collected on multiple bones and grouping the data by implant size, the method described herein can facilitate optimal design of the femoral stem on the femoral implant such that the stem can be adequately implanted in the canal of the patient's femur.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A method of designing a femoral component having a stem extension and configured for implantation on a distal end of a femur, the method comprising:
   determining a canal axis of a plurality of femurs using at least one cylinder to create an optimal fit between a reamer and a diaphysis of each of the plurality of femurs, the plurality of femurs having a comparable size and configured to correspond to one implant size of an implant family; and
   determining a position of the stem extension on the femoral component as a function of the determined canal axis of the plurality of femurs.

2. The method of claim 1, wherein the position of the stem extension on the femoral component is determined by measuring a distance between the canal axis and an anterior cortex in a distal cut plane for each of the plurality of femurs.

3. The method of claim 1, wherein the position of the stem extension on the femoral component can be determined for each of the plurality of femurs and averaged to determine the position of the stem extension on the femoral component for a particular size in the implant family.

4. The method of claim 1, wherein determining the canal axis of the plurality of femurs includes adjusting a distal entry point for insertion of the at least one cylinder.

5. The method of claim 1, wherein determining the canal axis of the plurality of femurs includes:
   (a) providing two or more cylinders having various diameters and representing reamers configured for use in preparing a femur for a femoral implant;
   (b) inserting a first cylinder, having a first diameter, into a canal of the femur to a predetermined reaming depth;

(c) if a reaming depth achievable with the first cylinder is less than the predetermined reaming depth, inserting the first cylinder into the canal to a maximum reaming depth that the first cylinder is able to fit in the canal; and (d) if the reaming depth achievable is about equal to or greater than the predetermined reaming depth and the first cylinder is not seated against an inner cortex of the femur, inserting a second cylinder, having a second diameter, into the canal of the femur to the predetermined reaming depth, the second diameter being greater than the first diameter of the first cylinder;

(e) repeating step (d) using cylinders of increasingly greater diameters, until a particular cylinder is seated in the canal; and (f) determining an optimal cylinder position based on step (c) or (e), wherein an optimal canal axis is based on a longitudinal axis of the optimal cylinder position.

6. The method of claim 5, wherein step (f) of determining the optimal cylinder position includes adjusting an entry point for inserting the particular cylinder in the distal end of the femur in at least one of an anterior/posterior direction and a medial/lateral direction.

7. The method of claim 5, further comprising repeating step (c) by reducing the reaming depth by increments of 5 mm.

8. The method of claim 5, wherein repeating step (d) includes increasing a cylinder diameter by increments of 1 mm.

9. The method of claim 5, wherein the diameter of the first cylinder is 10 mm.

* * * * *